United States Patent
Asano (10) Patent No.: US 8,052,740 B2
(45) Date of Patent: Nov. 8, 2011

(54) STENT INCLUDING A MARKER FITTED TO A FRAME PORTION

(75) Inventor: Hiroyuki Asano, Kanagawa (JP)

(73) Assignee: Piolax Medical Devices, Inc., Yokohama-Shi, Kanagawa (JP)

( * ) Notice: Subject to any disclaimer, the term of this patent is extended or adjusted under 35 U.S.C. 154(b) by 26 days.

(21) Appl. No.: 12/449,455

(22) PCT Filed: Dec. 25, 2007

(86) PCT No.: PCT/JP2007/074786
§ 371 (c)(1),
(2), (4) Date: Aug. 7, 2009

(87) PCT Pub. No.: WO2008/096512
PCT Pub. Date: Aug. 14, 2008

(65) Prior Publication Data
US 2010/0324663 A1    Dec. 23, 2010

(30) Foreign Application Priority Data
Feb. 9, 2007    (JP) .............................. P2007-030716

(51) Int. Cl.
*A61F 2/82*    (2006.01)
(52) U.S. Cl. ..................... 623/1.34; 623/1.15
(58) Field of Classification Search ........ 623/1.15–1.17, 623/1.34, 1.42
See application file for complete search history.

(56) References Cited

U.S. PATENT DOCUMENTS

| 6,090,127 | A | * | 7/2000 | Globerman | 606/194 |
| 6,113,627 | A |   | 9/2000 | Jang |   |
| 6,402,777 | B1 | * | 6/2002 | Globerman et al. | 623/1.11 |
| 6,730,116 | B1 |   | 5/2004 | Wolinsky et al. |   |
| 2002/0143386 | A1 |   | 10/2002 | Davila et al. |   |
| 2003/0149469 | A1 |   | 8/2003 | Wolinsky et al. |   |
| 2003/0225448 | A1 | * | 12/2003 | Gerberding | 623/1.15 |
| 2004/0015228 | A1 |   | 1/2004 | Lombardi et al. |   |
| 2005/0085897 | A1 | * | 4/2005 | Bonsignore | 623/1.15 |

FOREIGN PATENT DOCUMENTS

| JP | 2002-541910 | 12/2002 |
| JP | 2003-527132 | 9/2003 |
| JP | 2004-506477 | 3/2004 |
| JP | 2004-524916 | 8/2004 |
| JP | 2005-527322 | 9/2005 |
| JP | 2005-279076 | 10/2005 |

\* cited by examiner

*Primary Examiner* — Thomas J Sweet
*Assistant Examiner* — Leslie Coburn
(74) *Attorney, Agent, or Firm* — McGinn IP Law Group, PLLC (57) ABSTRACT

A stent includes a plurality of annular units each made of a linear portion which extends circumferentially while folding in a zigzag manner and which is connected annularly, and connection portions which connect axially adjacent ones of the annular units with each other. Predetermined annular units have radiopaque markers each fixedly attached midway between one folded portion and a next folded portion in the linear portion located in a predetermined circumferential position.

20 Claims, 8 Drawing Sheets

STENT INCLUDING A MARKER FITTED TO A FRAME PORTION

FIELD OF THE INVENTION

The present invention relates to a stent which is indwelled in a tubular organ such as a blood vessel, a ureter, a bile duct, a trachea, etc., so as to prevent stenosis or obstruction of the tubular organ or rupture of an aneurysm or the like.

DESCRIPTION OF RELATED ART

In recent years, there has prevailed a treatment method using a stent, in which the stent is indwelled in a stenosed or obstructed portion in a tubular organ of a human body such as a blood vessel, a ureter, a bile duct, a trachea, etc., so as to expand the stenosed or obstructed portion, or the stent is indwelled in a portion where an aneurysm has occurred, so as to prevent rupture of the aneurysm.

To indwell the stent in a predetermined indwelling position, the stent is contracted radially and received, for example, in a medical tube. After the tube is moved to the indwelling position, the stent is pushed out from the tube by a pusher or the like. In this manner, the stent is indwelled. In addition, a stent provided with markers made of a radiopaque material may be used to confirm the position of the stent in a tubular organ.

As the aforementioned stent provided with radiopaque markers, the undermentioned Patent Document 1 has disclosed a stent having a cylindrical shape as a whole, in which a plurality of annular bodies formed in a zigzag manner are connected axially by connection portions. Further, rectangular pieces extend axially outward from folded portions which are located in axially outer sides of the annular bodies located in the opposite ends of the stent. An annular marker housing is connected to the rectangular pieces. Markers are inserted and attached into the housing.

In addition, the undermentioned Patent Document 2 has disclosed a stent having a cylindrical shape, in which a plurality of annular bodies formed in a zigzag manner are connected axially by connection portions in the same manner as in the aforementioned Patent Document 1. Further, substantially T-shaped carrier portions are provided to extend axially outward from folded portions which are located in axially outer sides of the opposite ends of the stent. Substantially U-shaped markers are fitted and attached to the outer circumferences of the carrier portions.

Further, the undermentioned Patent Document 3 has disclosed a stent having a cylindrical shape as a whole, in which a plurality of annular bodies formed in a zigzag manner are connected axially by connection portions in the same manner as in the aforementioned Patent Document 1 or 2. Markers are provided in the connection portions.

Patent Document 1: JP-T-2004-524916
Patent Document 2: JP-T-2004-506477
Patent Document 3: JP-A-2005-279076

BRIEF SUMMARY OF THE INVENTION

Problems that the Invention is to Solve

In the case of the stent according to the aforementioned Patent Document 1 or 2, the markers protrude outward from the opposite end portions of the stent. However, in such a stent where the markers protrude from the opposite ends, a marker protruding portion having no expansion force serves as a leading end of the stent. Thus, there is a case where a portion contributing to expansion of the leading end cannot be inserted to reach a deeper place of an obstructed or stenosed portion of a tubular organ. As a result, the expansion force of the stent cannot be given to the deeper place of the obstructed or stenosed portion. Thus, there occurs a fear that the indwelling effect of the stent may be reduced.

In addition, the stent is designed to be bent due to the connection portions as the stent is inserted into a bent tubular organ. However, in the stent disclosed in the aforementioned Patent Document 3, the markers are provided in the connection portions. Thus, the flexibility of the connection portions is too low so that it is difficult to bend the stent. In addition, there occurs a fear that the stent may be folded down and kinked in the connection portions.

An object of the present invention is therefore to provide a stent which can indwell surely up to a deeper place of an obstructed or stenosed portion of a tubular organ so as to exhibit the expansion force thereof while also keeping the flexibility.

Means for Solving the Problems

In order to attain the foregoing object, according to a first aspect of the present invention, there is provided a stent including a plurality of annular units each made of a linear portion which extends circumferentially while folding in a zigzag manner and which is connected annularly, and connection portions which axially connect the annular units with each other, the stent being characterized in that at least one of the annular units has a radiopaque marker which is fixedly attached midway between a folded portion and a next folded portion in the linear portion located in a predetermined circumferential position.

According to the aforementioned aspect of the invention, the radiopaque marker is fixedly attached midway between a folded portion and a next folded portion in the linear portion located in a predetermined circumferential position in at least one of the annular units. Accordingly, it is unnecessary to provide a portion protruding from an end portion of the stent. Thus, the annular unit located in the end portion of the stent can be inserted to reach a deeper place of an obstructed or stenosed portion of a tubular organ of a human body, so that an expansion force can be given to the deeper place of the obstructed or stenosed portion of the tubular organ. In addition, since the radiopaque marker is fixedly attached midway between a folded portion and a next folded portion in the linear portion forming the annular unit, the flexibility of the stent is secured without spoiling the flexibility in each folded portion of the linear portion so that the stent can be operated to be inserted into the tubular organ smoothly.

According to a second aspect of the present invention, there is provided a stent defined in the aforementioned first aspect of the invention, wherein a frame portion is provided in the midway between the folded portion and the next folded portion in the linear portion, and the marker is fitted and fixedly attached to the frame portion.

According to the aforementioned aspect of the invention, the marker is fitted and fixedly attached to the frame portion. The marker is therefore difficult to drop out. In addition, since the marker is fitted to the frame portion, it is easy to reduce protrusion of the marker to thereby make the surface flat. When the stent is indwelled in a tubular organ, it is possible to prevent the stent from damaging the inner wall of the tubular organ.

According to a third aspect of the present invention, there is provided a stent defined in the aforementioned second aspect of the invention, wherein the frame portion provided in the midway between the folded portion and the next folded portion in the linear portion has an elliptic shape with a major axis and a minor axis, and a direction of the major axis is disposed substantially along a length direction of the linear portion.

According to the aforementioned aspect of the invention, the width of the linear portion to which the marker is fixedly attached can be made as narrow as possible, while a large area can be secured for the portion where the marker is fixedly attached. It is therefore possible to reduce the width of the linear portion without lowering the visibility of the marker, so that it is possible to increase the number of folds in the linear portion of the annular unit having the marker.

According to fourth and fifth aspects of the present invention, there is provided a stent defined in the aforementioned second or third aspect of the invention, wherein the linear portion provided with the frame portion is connected tangentially to the frame portion so that an angle of each folded portion can be made as small as possible.

According to the aforementioned aspects of the invention, it is possible to reduce the angle of each folded portion of the linear portion provided with the frame portion, so that it is possible to enhance the expansibility of the annular unit having the marker.

According a sixth aspect of the present invention, there is provided a stent defined in the aforementioned first aspect of the invention, wherein an axial length of any annular unit that has the marker is made longer than an axial length of any annular unit that does not have the marker.

In an annular unit having a marker, a linear portion in a portion where the marker is fixedly attached should be so wide that the number of circumferentially zigzagged folds must be reduced. Therefore, when the axial interval of each linear portion between a folded portion and a next folded portion is constant, the annular unit cannot be expanded to have the same outer diameter as that of another annular unit unless the open angle of each folded portion in the annular unit is made larger than that in another annular unit.

However, when the axial length of any annular unit that has the marker is made longer than the axial length of any annular unit that does not have the marker as in the aforementioned aspect of the invention, the circumferential expansion of the annular unit having the marker can be increased in spite of a small open angle of each folded portion. Thus, the open angle can be made close to the open angle of each folded portion in the annular unit that does not have the marker. It is therefore possible to give a uniform expansion force over the whole length of the stent. In addition, the annular unit can be expanded in spite of a small open angle of each folded portion in its linear portion. It is therefore possible to reduce shortening (axial shortening) in the expansion state.

According to a seventh aspect of the present invention, there is provided a stent defined in the aforementioned first aspect of the invention, wherein the annular units each having the marker are disposed in axially opposite end portions of the stent.

According to the aforementioned aspect of the invention, the markers are provided in the axially opposite end portions of the stent. Accordingly, it is possible to grasp the positions of the opposite end portions of the stent accurately.

According to an eighth aspect of the present invention, there is provided a stent defined in the aforementioned first aspect of the invention, wherein the annular unit having the marker is disposed in an axially intermediate portion of the stent.

According to the aforementioned aspect of the invention, the position of the intermediate portion of the stent can be confirmed surely. As a result, when, for example, it is intended to dispose the intermediate portion of the stent in a branch portion of a tubular organ, dispose one end of the stent in the tubular organ on its proximal portion side and dispose the other end of the stent in one of tubular organs branching from the branch portion, it is possible to make it easy to position the stent. In addition, when it is intended to indwell another stent in a tubular organ branching from a branch portion, one stent is indwelled with its intermediate portion in line with the branch portion in advance. Another stent is inserted from the tubular organ branching from the branch portion, and the leading end portion of the other stent is inserted into the indwelled stent through a gap in a linear portion of the intermediate portion of the indwelled stent. Thus, the other stent can be indwelled in the branching tubular organ. In this manner, when it is intended to insert another stent into another branching tubular organ, the intermediate portion of a stent which has been already indwelled can be recognized visibly due to the marker. Thus, operations can be made easier.

Effect of the Invention

According to a stent of the present invention, a radiopaque marker is fixedly attached midway between a folded portion and a next folded portion in a linear portion forming an annular unit. It is therefore unnecessary to provide a portion protruding from an end portion of the stent. Thus, an annular unit located in the end portion of the stent can be inserted up to a deeper place than an obstructed portion of a tubular organ, and an expansion force can be given to the deeper place. In addition, since the radiopaque marker is provided in the aforementioned position, the flexibility of the stent is secured without jeopardizing the flexibility in each folded portion of the linear portion so that the stent can be operated to be inserted into the tubular organ smoothly.

BRIEF DESCRIPTION OF THE DRAWINGS

FIG. 7 Views showing the state of the stent in a process of indwelling the stent in a tubular organ, in which: (a) is an explanatory view in a first step of the process; (b) is an explanatory view in a second step of the process; and (c) is an explanatory view in a third step of the process.

DETAILED DESCRIPTION OF THE INVENTION

Best Mode for Carrying Out the Invention

An embodiment of a stent according to the present invention will be described below with reference to the drawings.

The material of a stent 1 according to the present invention is not limited particularly, but metal such as stainless steel, Ta, Ti, Pt, Au, W, etc. or a shape memory alloy of an Ni—Ti base, a Cu—Al—Ni base, a Cu—Zn—Al base, etc. can be preferably used.

A method for manufacturing the stent 1 according to the present invention is not limited particularly. However, for example, the stent 1 can be manufactured by producing a cylindrical body of a predetermined size out of the aforementioned metal, and cutting the cylindrical body into a predetermined pattern by means of etching, laser machining, or the like. When a shape memory alloy or the like is used, the cutting shape is produced as a radially contracted shape, and the cut cylindrical body is radially expanded and subjected to shape memory treatment. Thus, the cylindrical body can be brought into an expanded state.

Figure 1:
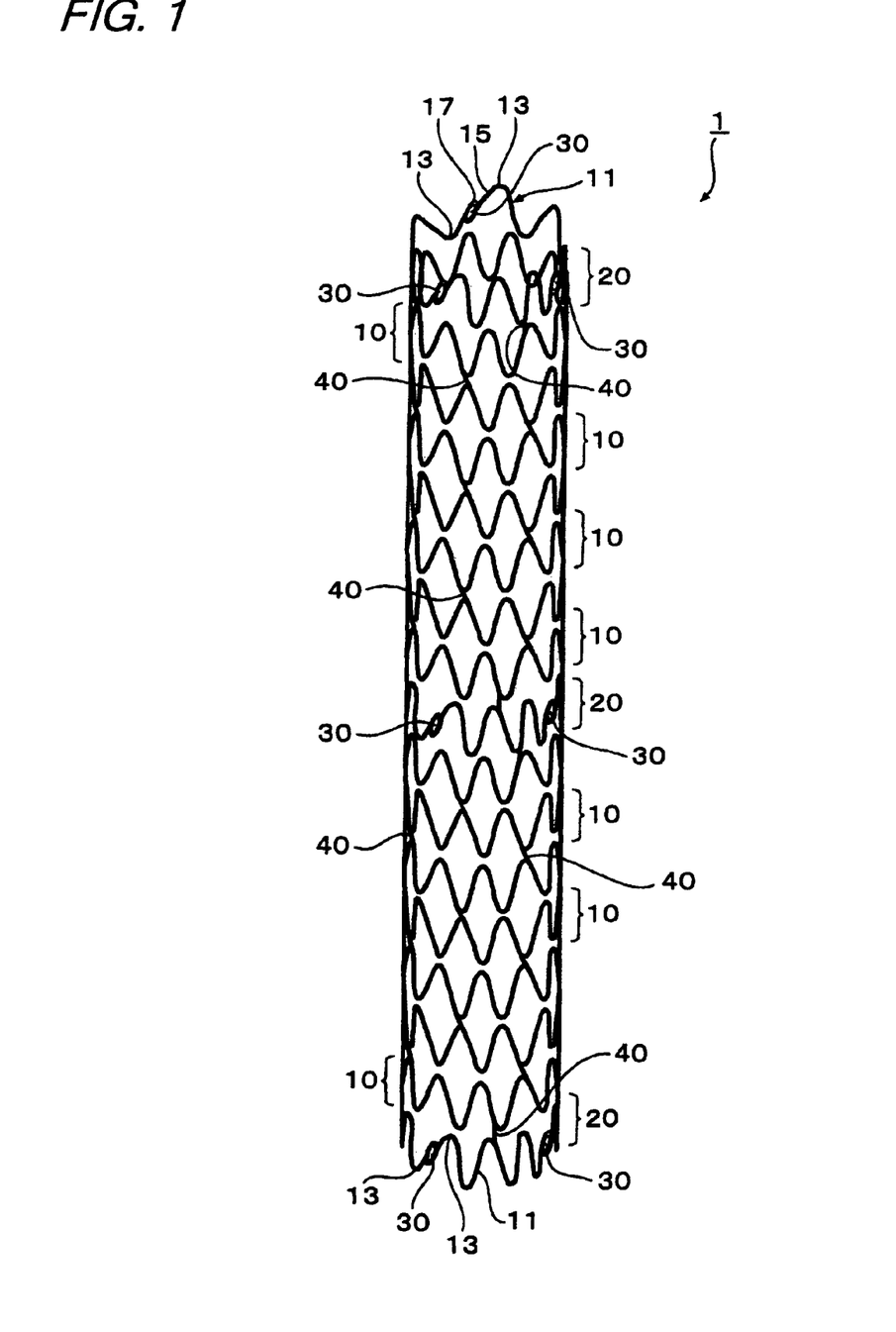
FIG. 1 A perspective view showing an embodiment of a stent according to the present invention in an expanded state.
Figure 2:
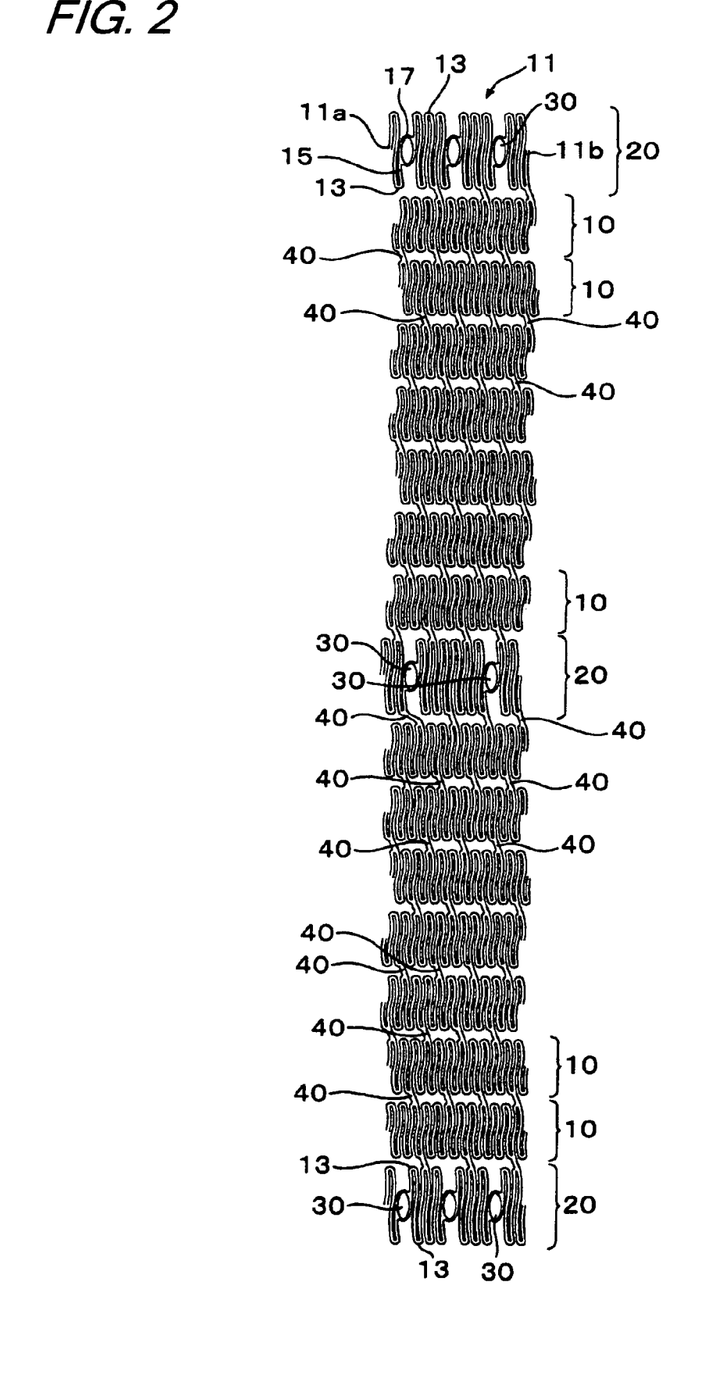
FIG. 2 A development of the stent in a radially contracted state.
Figure 3:
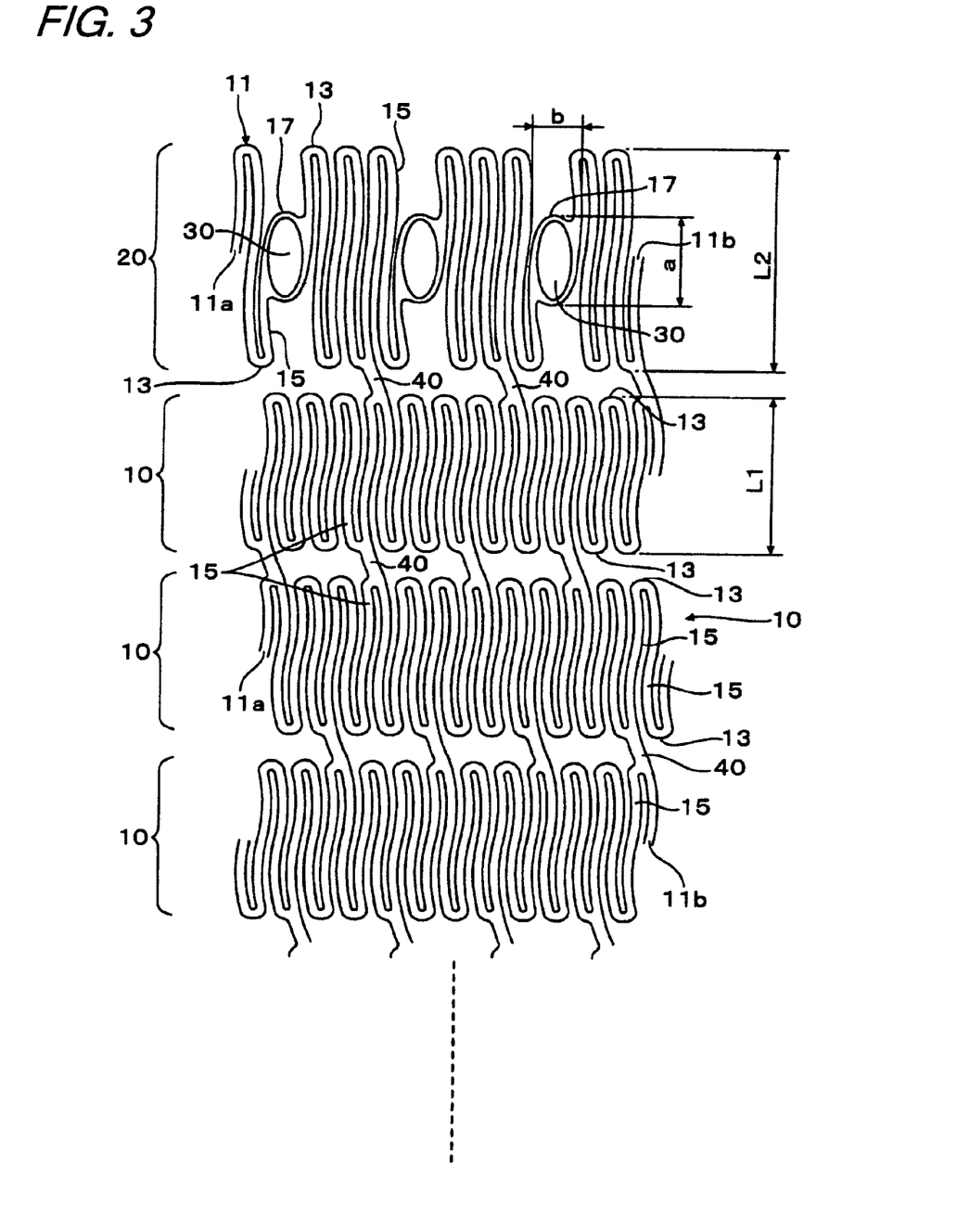
FIG. 3 A main portion enlarged view of FIG. 2.
Figure 4:
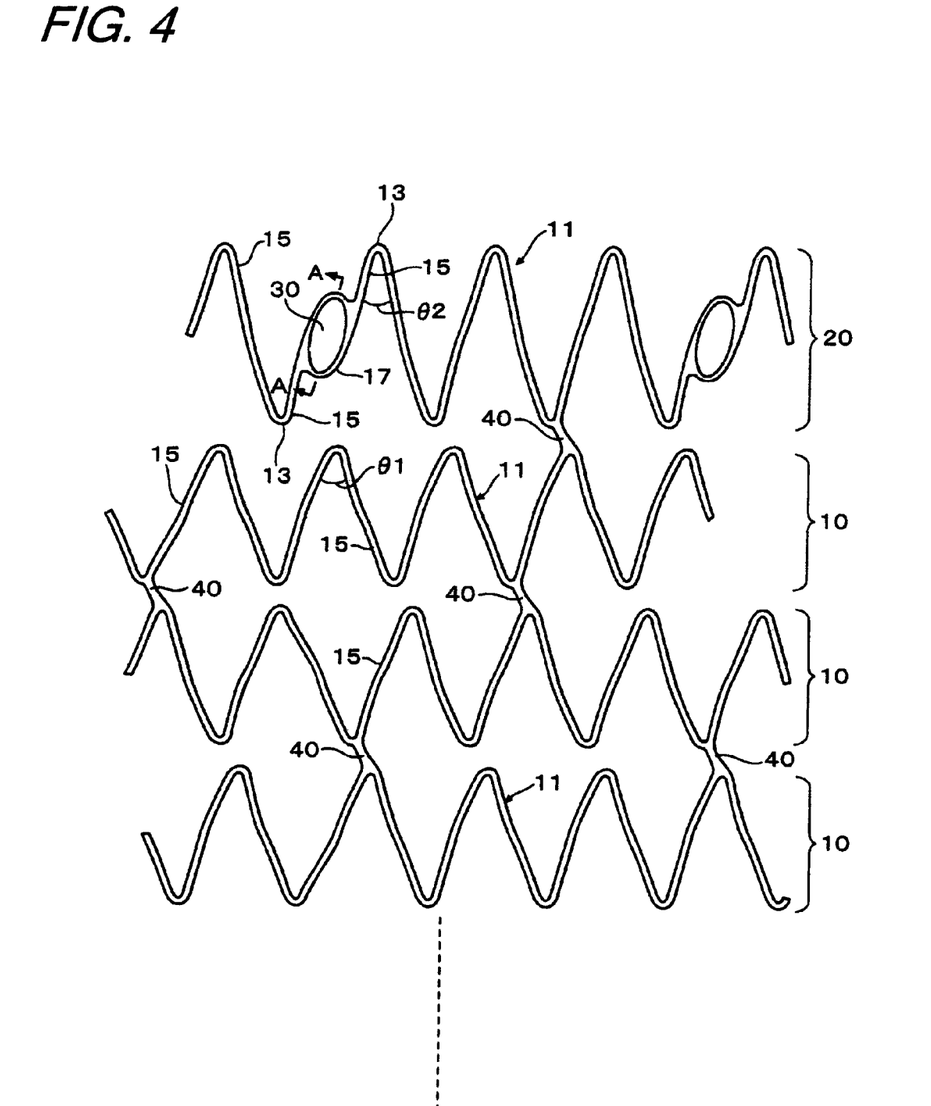
FIG. 4 An enlarged view of a main portion of the stent according to the present invention in an expanded state.

The stent 1 is normally expanded (see FIGS. 1 and 4). When the stent 1 is received in a catheter or the like in order to indwell in a predetermined indwelling place of a tubular organ, the stent 1 is radially contracted (see FIGS. 2, 3 and 6). FIGS. 2 and 3 show the state where the stent 1 is radially contracted, and also show the shape with which the metal cylindrical body is cut when the aforementioned manufacturing method is used.

The stent 1 according to the present invention includes a plurality of annular units arrayed axially. At least one of the annular units is provided with radiopaque markers 30. That is, as shown in FIG. 1, the stent 1 has normal annular units 10 each having no marker 30 and annular units 20 each having the markers 30. The annular units 10 and 20 are arrayed axially, and adjacent ones of the annular units are connected by connection portions 40. In addition, in this embodiment, the annular units 20 having the markers 30 are disposed in axially opposite end portions and an axially intermediate portion of the stent 1.

FIG. 2 shows a development where the stent 1 is radially contracted. FIG. 3 shows an enlarged view of a main portion of FIG. 2. Referring to these drawings, each of the annular units 10 and 20 includes a linear portion 11 which extends circumferentially while bending like waves and folding in a zigzag manner and which is connected annularly. In the developments shown in FIGS. 2 and 3, a leading end portion 11a and a trailing end portion lib of the linear portion 11 are separated for the sake of convenience. In fact, as shown in FIG. 1, the leading end portion 11a and the trailing end portion lib are connected to each other so that the linear portion 11 has an annular shape.

The zigzag pattern of the linear portion 11 forming each annular unit 10, 20 has folded portions 13 each having an arcuate shape, and intermediate portions 15 each located between one folded portion 13 and the next folded portion 13. In the state where the stent 1 is radially contracted as shown in FIGS. 2 and 3, each intermediate portion 15 has a gentle S-shape. Further, each intermediate portion 15 is disposed substantially along the axis direction of the stent 1.

In addition, as described previously, of the two kinds of annular units 10 and 20, each annular unit 20 is provided with radiopaque markers 30. The stent 1 according to the present invention is characterized in that each marker 30 is provided not in the outside of the folded portion 13 as in a background-art stent but in the intermediate portion 15.

That is, as shown in FIG. 3, each marker 30 is fixedly attached to the midway of the intermediate portion 15 between one folded portion 13 and the next folded portion 13 in the linear portion 11 located in a predetermined circumferential position of the annular unit 20. Specifically, a frame portion 17 having a predetermined shape is provided at the lengthwise center of the intermediate portion 15 between one folded portion 13 and the next folded portion 13, and the marker 30 is fitted and fixedly attached to the inside of the frame portion 17.

In this embodiment, the frame portion 17 has a substantially elliptic shape with a major axis a and a minor axis b. At the same time, when the stent 1 is radially contracted, the frame portion 17 is disposed so that its major axis runs substantially along the lengthwise direction of the linear portion 11. In addition, opposite side pieces of the intermediate portion 15 where the frame portion 17 is provided are connected substantially tangentially to the frame portion 17 so that the open angle of the folded portion 13 connected by those pieces becomes as small as possible when the stent is expanded. That is, the intermediate portions 15 connected to the opposite sides of the marker 30 extend substantially in parallel at a gap where the frame portion 17 can be inserted, and are connected tangentially to the opposite outer circumferential portions of the frame portion 17 respectively (see FIG. 3).

Figure 5A:
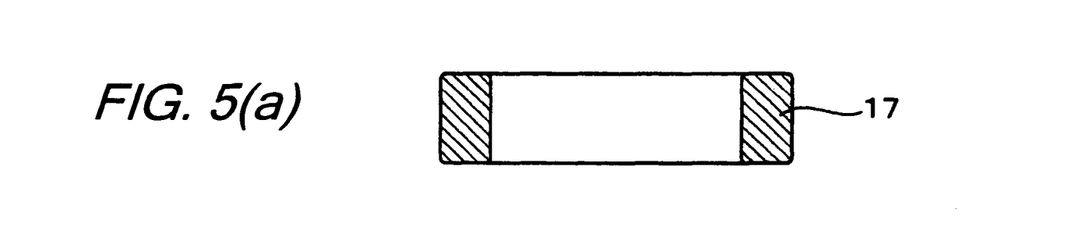
FIG. 5 Sectional views taken on line A-A in FIG. 4.
Figure 5B:
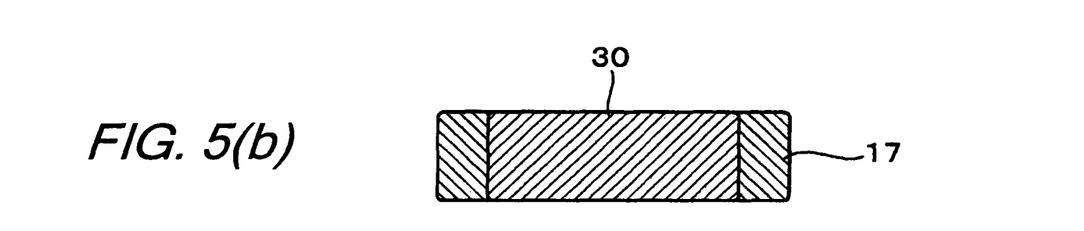
Figure 5C:
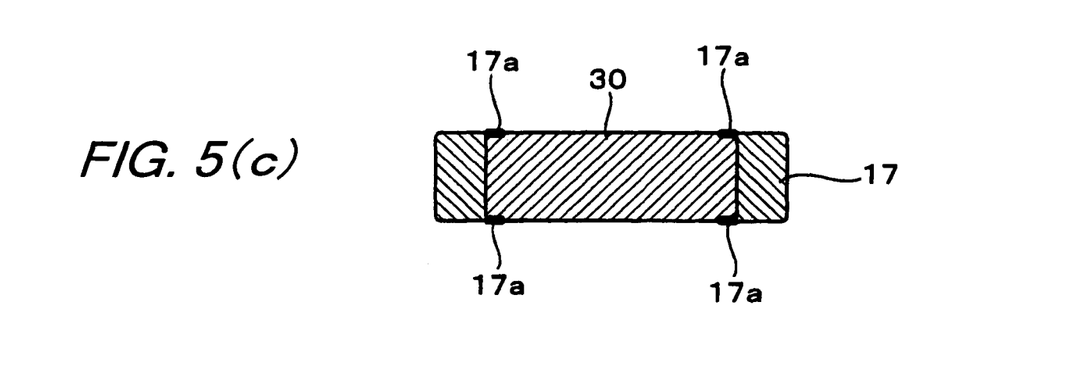

Then, the marker 30 is fitted to the frame portion 17 so as to be fixedly attached thereto. The marker 30 is made of a radiopaque metal material consisting of Au, Pt, Pd, Ta, W, an alloy of those metals, or the like. In this embodiment, the marker 30 is formed into an elliptic flake which can be fitted to the inner circumference of the frame portion 17. FIGS. 5(a) to (c) show the process for fixedly attaching the marker 30 to the frame portion 17. That is, as shown in FIG. 5(a), a predetermined part of a metal cylinder is cut into an elliptic shape to form the frame portion 17. As shown in FIG. 5(b), the marker 30 is fitted to the inner circumference of the frame portion 17. After that, upper and lower circumferential edge portions of the frame portion 17 are irradiated with a laser from a predetermined direction so as to be fused to form drop-out prevention protrusions 17a which can engage with the upper and lower opposite surfaces of the marker 30 as shown in FIG. 5(c). By the drop-out prevention protrusions 17a, the marker 30 is fixed to the frame portion 17 and prevented from dropping out, so as to be fixedly attached to the annular unit 20. The marker 30 may be fixed and prevented from dropping out, for example, by swaging the circumferential edge of the frame portion 17. The fixing method is not limited particularly.

Further, as described previously, the annular units 20 having the markers 30 are disposed in the axially opposite end portions and the axially intermediate portion of the stent 1. On this occasion, in each of the annular units 20 in the opposite end portions of the stent 1, markers 30 are fixedly attached to three frame portions 17 disposed at equal circumferential intervals, respectively. On the other hand, in the annular unit 20 in the intermediate portion of the stent 1, two frame portions 17 are provided in circumferential opposition to each other, and markers 30 are fixedly attached thereto (see FIG. 2).

In each annular unit 20 having the markers 30, the linear portion 11 to which the markers 30 are fixedly attached becomes wider than that in each annular unit 10 having no marker 30. As a result, the number of folded portions 13 of the zigzag pattern running along the circumferential direction of the linear portion 11 becomes small. In this embodiment, the number of folded portions 13 in each annular unit 10 is 12, and the number of folded portions 13 in each annular unit 20 is nine. In order to expand the outer diameter of the stent 1 uniformly, the open angle of each folded portion 13 in the annular unit 20 must be made larger than the open angle of each folded portion 13 in the annular unit 10. It is therefore difficult to obtain a uniform expansion force in the axial direction. Due to the increased open angle of each folded portion 13, there occurs a problem that shortening may occur easily (so that the stent may be shortened axially when it is expanded).

To solve this problem, in this embodiment, the axial length L2 of each annular unit 20 having the markers 30 is set to be longer than the axial length L1 of each annular unit 10 having no marker 30 (L2>L1) as shown in FIG. 3. As a result, in the annular unit 20 having the markers 30, the intermediate portion 15 becomes so long that the annular unit 20 can expand largely in spite of a comparatively small open angle θ2 of each folded portion 13 when the stent 1 expands, as shown in FIG. 4. Accordingly, when the stent 1 is expanded axially with a substantially uniform outer diameter, the open angle θ2 of each folded portion 13 in the annular unit 20 having the markers 30 can be made as close to the open angle θ1 of each folded portion 13 in the annular unit 10 having no marker 30. Thus, an expansion force can be made substantially uniform in the axial direction of the stent 1, and it is also possible to suppress shortening. In this embodiment, the length L1 and the length L2 are adjusted to make the open angle θ2 of each folded portion 13 in the annular unit 20 substantially equal to the open angle θ1 of each folded portion 13 in the annular unit 10. The ratio of the length L2 to the length L1 may be determined suitably, for example, based on the respective numbers of the folded portions 13 in the annular units 10 and 20. It is generally preferable to set the ratio in a range expressed by L1:L2=1:1.2-1.6.

In addition, each annular unit is connected to annular units adjacent thereto in the axial direction of the stent 1 through a plurality of connection portions 40 which are disposed at circumferentially equal intervals. Each of the connection portions 40 is connected clear of the apex (center of bent portion) of each folded portion 13 and at a position slightly laterally displaced therefrom, as shown in FIGS. 3 and 4. That is, one intermediate portion 15 located on one side of one folded portion 13 extends linearly as it is, and is connected to another intermediate portion 15 located on one side of a corresponding folded portion 13 of another adjacent annular unit, so that the intermediate portions 15 of the adjacent annular units connected to each other through a connection portion 40 are connected to each other to form a gently curved linear shape. In addition, as shown in FIGS. 2 and 3, the connection portions 40 are arrayed in each annular unit so that the circumferential positions of the connection portions 40 are circumferentially shifted from those of the connection portions in another axially adjacent annular unit step by step.

In addition, it is preferable that the stent 1 is set to be 120-250 μm thick in order to be able to exhibit an expansion force strong enough to expand the diameter of a stenosed portion or the like of a tubular organ while preventing flexibility from being lowered at the time of insertion.

Next, description will be made on how to use the stent 1 according to the present invention.

Figure 6:
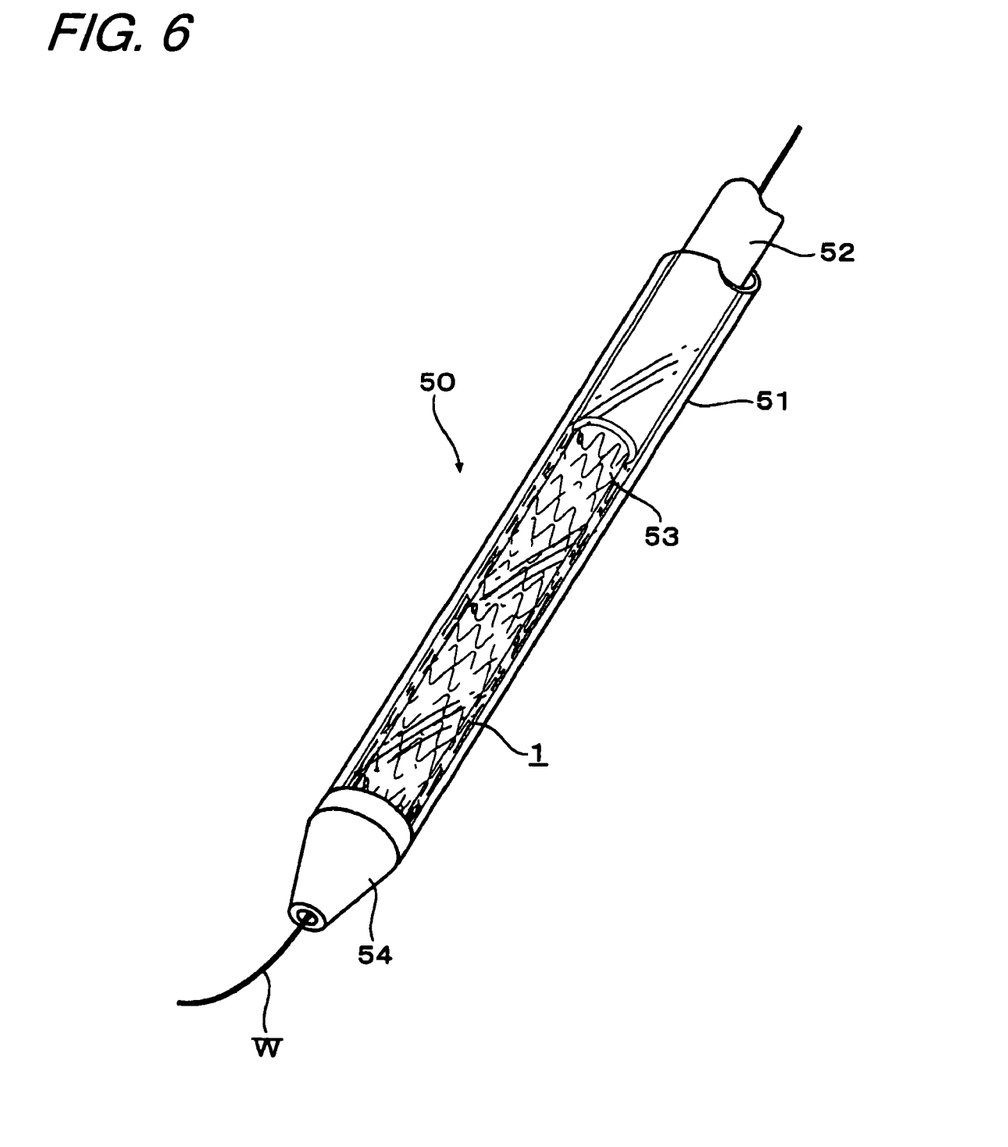
FIG. 6 A perspective view showing a state in which the stent according to the present invention has been received in a transport tool.

The stent 1 is transported to an intended indwelling place of a tubular organ, for example, by a transport tool 50 shown in FIG. 6. The transport tool 50 has an outer tube 51 and an inner tube 52 slidably inserted into the outer tube 51. A step portion 53 whose diameter is made smaller than on the proximal portion side is formed in the outer circumference of the inner tube 52 on its leading end side. A leading end portion of the inner tube 52 protrudes from a leading end portion of the outer tube 51. A tapered head portion 54 whose diameter is made larger than the inner diameter of the outer tube 51 is fitted to the leading end portion of the inner tube 52.

The stent 1 is radially contracted so as to bring its one end portion into contact with the proximal end surface of the step portion 53 of the inner tube 52 while bringing the other end portion into contact with a trailing end portion of the head portion 54. In this state, the outer tube 51 is slid to cover the outer circumference of the stent 1. Thus, the stent 1 radially contracted is received in the leading end portion of the transport tool 50. At this time, the stent 1 is radially contracted by folding the linear portions 11 so that the intermediate portions 15 on the opposite sides of each folded portion 13 approach each other with the folded portion 13 as the center.

Figure 7A:
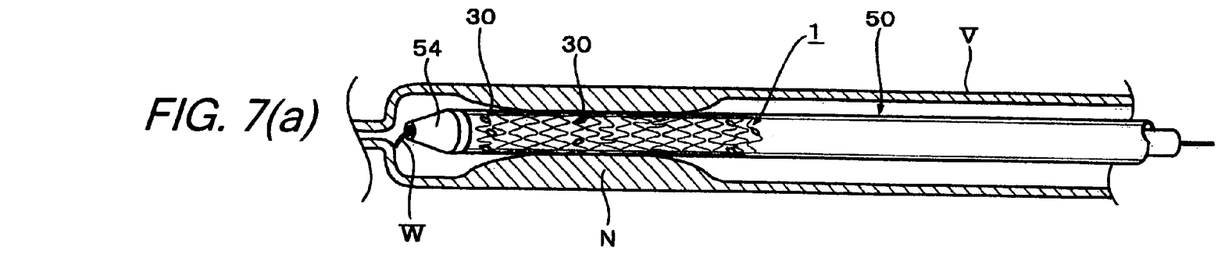
Figure 7B:
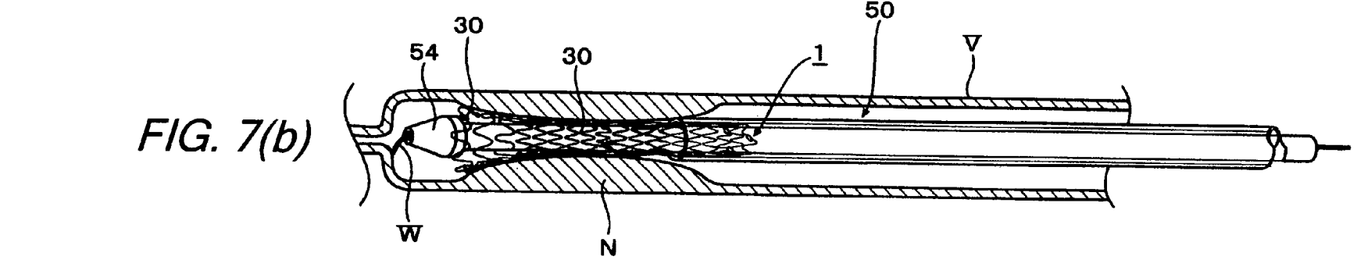
Figure 7C:
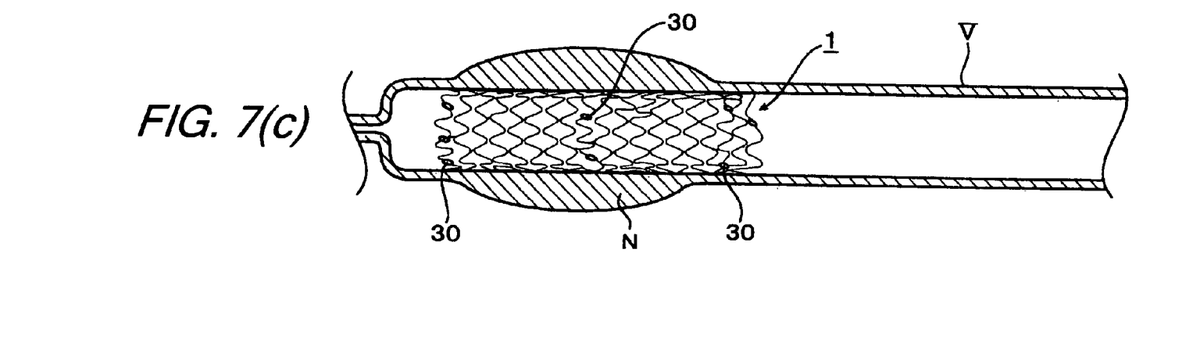

When the stent 1 has been received as described above, the transport tool 50 is inserted into a tubular organ V as shown in FIGS. 7(a) to 7(c). On this occasion, a not-shown sheath is inserted into the tubular organ V percutaneously. A guide wire W is inserted into the sheath from its proximal end so as to allow its leading end portion to reach a place a little deeper than a stenosed portion N which is the intended indwelling place.

In that state, the transport tool 50 is inserted from the proximal end portion of the guide wire W. The transport tool 50 is further moved along the outer circumference of the guide wire W, so that the head portion 54 at the leading end of the transport tool 50 reaches a slightly deeper place than the stenosed portion N as shown in FIG. 7(a). In this example, the deeper side of the stenosed portion N is a blind end where the inner diameter of the tubular organ is extremely narrowed. The leading end of the transport tool 50 is inserted to reach the blind end.

The aforementioned operation for inserting the transport tool 50 is performed based on radiopaque portions which are made visible by irradiation with X-rays. Then, a predetermined position of the transport tool 50 is brought into line with the predetermined position of the intended indwelling place which has been made visible by X-rays due to a contrast medium injected thereto in advance. Thus, the stent 1 is positioned.

If a background-art stent provided with a marker protruding outward from its end portion is used, the position of a circumferential unit having an expansion force will be separated from the blind end correspondingly to the protruding portion of the marker. Thus, it is likely that the circumferential unit having the expansion force cannot be disposed in a portion close to the blind end of the stenosed portion N.

On the other hand, according to the stent 1 of the present invention, each radiopaque marker 30 is fixedly attached to the intermediate portion 15 between one folded portion 13 and the next folded portion 13 in the linear portion 11 located at a predetermined circumferential position of each annular unit 20. It is therefore unnecessary to provide any portion protruding from the end portion of the stent 1. It is therefore possible to insert the annular unit 20 located in the end portion of the stent 1 surely up to a deeper place than the stenosed portion N of the tubular organ V.

Then, in this state, the proximal end portion side of the inner tube 52 is fixed, and the outer tube 51 is pulled back and slid. As a result, as shown in FIG. 7(b), the stent 1 is gradually released from the leading end portion of the outer tube 51 so that each annular unit 10, 20 is radially expanded. When the outer tube 51 is further slid, the stent 1 is perfectly released so that the stenosed portion N is pushed from inside and expanded as shown in FIG. 7(c). Thus, the stent 1 is indwelled in the state where the stenosed portion N is expanded.

At that time, in the stent 1 according to the present invention, as described above, the annular unit 20 in the end portion of the stent 1 is inserted up to the deeper place than the stenosed portion N, so that the end portion of the stent 1 is firmly positioned at the deeper end portion of the stenosed portion N. Accordingly, the expansion force of the stent 1 can be applied over the whole length of the stenosed portion N so that the treatment effect on the stenosed portion N can be enhanced.

In addition, in the stent 1 according to the present invention, each marker 30 is fixedly attached to the intermediate portion 15 between one folded portion 13 and the next folded portion 13 in the linear portion 11 forming the annular unit 20. Accordingly, the flexibility in each folded portion 13 of the linear portion 11 is not jeopardized, but the flexibility of the stent 1 can be secured. Thus, even when the stent 1 is inserted into a largely curved tubular organ, a tubular organ having a plurality of irregularities in its inner wall, or the like, the stent 1 can be inserted smoothly without being folded down and kinked. In addition, the transport tool 50 etc. for receiving the stent 1 can be also operated easily.

When the stent 1 is released from the transport tool 50, the folded portions 13 of the annular units 10 and 20 are open at predetermined open angles θ1 and θ2 respectively as shown in FIG. 4, so that the stent 1 is radially expanded. At this time, the axial length L2 of each annular unit 20 having the markers 30 is longer than the axial length L1 of each annular unit 10 having no marker 30. Therefore, the open angle θ2 of each folded portion 13 in the annular unit 20 can be made close to the open angle θ1 of each folded portions 13 in the annular unit 10, so that a uniform expansion force can be given to the whole length of the stent 1. In addition, even if the open angle of each folded portion 13 in the linear portion 11 is small, the linear portion 11 can be expanded. It is therefore possible to reduce shortening (axial shortening) in the expansion state.

In addition, each marker 30 is fitted to the frame portion 17 having an elliptic shape, and fixed and prevented from dropping out by the drop-out prevention protrusion 17a (see FIG. 5). Thus, the marker 30 can be surely prevented from dropping out. Further, since the marker 30 is fitted to the frame portion 17, the protrusion of the marker 30 is reduced, and the surface thereof can be easily made flat. It is therefore possible to prevent the inner wall of the tubular organ V from being damaged when the stent 1 is indwelled in the tubular organ V.

Further, since the frame portion 17 has an elliptic shape, the width of the linear portion 11 where the marker 30 is fixedly attached can be made as narrow as possible, while a large area can be secured for the portion where the marker is fixedly attached. Accordingly, the width of the linear portion 11 can be narrowed without lowering the visibility of the marker 30. Thus, the number of folds in the linear portion 11 of each annular unit 20 having the markers 30 can be increased.

Figure 8:
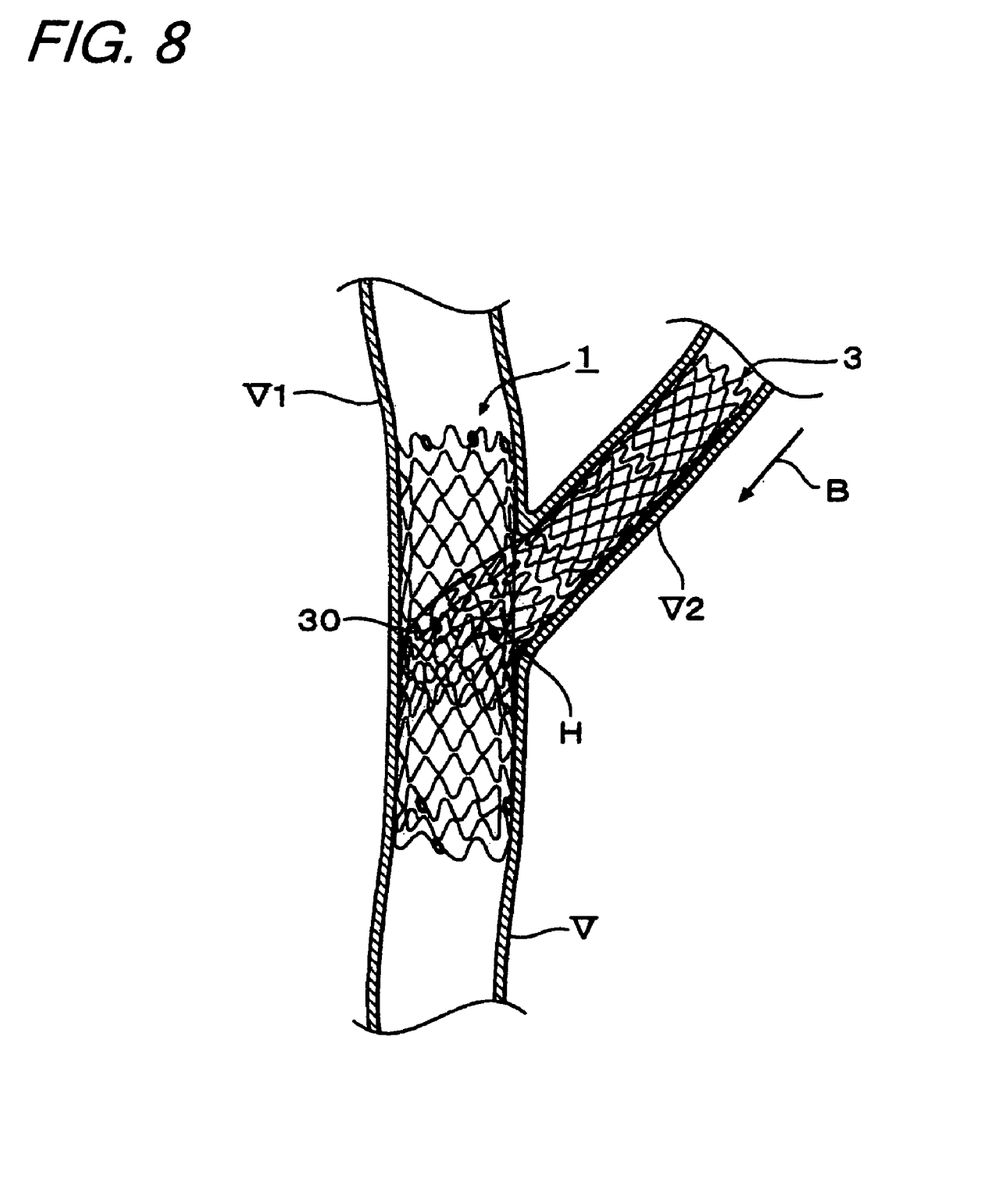
FIG. 8 An explanatory view showing the state where the stent has been indwelled in a branch portion of the tubular organ.

FIG. 8 shows another use mode of the stent 1. That is, since the annular unit 20 having the markers 30 is provided in the axially intermediate portion of the stent 1 according to this embodiment, the position of the intermediate portion can be confirmed surely. Accordingly, even when the tubular organ has two branch vessels V1 and V2 branching therefrom as shown in FIG. 8, it is possible to indwell the stent easily.

That is, assume that it is intended to dispose the intermediate portion of the stent 1 in a branch portion H, dispose one end of the stent 1 in the tubular organ V on its proximal portion side and dispose the other end of the stent 1 in the branch vessel V1. In this case, the markers 30 are provided in the intermediate portion of the stent 1 as described above, so that the stent 1 can be positioned and indwelled easily.

In addition, it may be intended to indwell another stent in the other branch vessel V2. In this case, the stent 1 is indwelled in such a manner that the intermediate portion is brought into line with the branch portion H with reference to the markers 30 as described above, and one end is disposed in the tubular organ V while the other end is disposed in the branch vessel V1. In that state, another transport tool 50 where another stent 3 is received in its leading end portion is inserted into the branch vessel V2 from the direction designated by the arrow B in FIG. 8, so as to be inserted into the indwelled stent 1 through a gap of the linear portion 11 in the intermediate portion of the indwelled stent 1. Further, the transport tool 50 is moved so that the leading end portion thereof is positioned on the tubular organ V side of the stent 1. In that state, the outer tube 51 is slid back. As a result, the stent 3 is released gradually so that its leading end portion side is expanded substantially with the same outer diameter as the outer diameter of the stent 1 which has been already indwelled, while its proximal end portion side is expanded in the branch vessel V2. Thus, the other stent 3 can be indwelled in the branch vessel V2.

In this manner, when another stent 3 is indwelled in the branch vessel V2, the intermediate portion of the stent 1 set in advance can be recognized visibly due to the markers 30. Thus, operation can be carried out based on the markers 30 so that the other stent 3 can be indwelled easily.

The invention claimed is:

1. A stent comprising:
a plurality of annular units each made of a linear portion which extends circumferentially while folding in a zig-zag manner and which is connected annularly; and
connection portions which axially connect the annular units with each other,
wherein at least one of the annular units is provided with an elliptically shaped frame portion midway between a folded portion and a next folded portion in the linear portion located in a predetermined circumferential position,
wherein the linear portion connected to the frame portion is connected tangentially to opposite outer circumferential portions of the frame portion so that an angle of each folded portion becomes as small as possible,
wherein a radiopaque marker is fitted and fixedly attached to the frame portion,
wherein the frame portion provided midway between the folded portion and the next folded portion in the linear portion comprises an elliptic shape with a major axis and a minor axis, and
wherein a direction of the major axis is disposed substantially along a length direction of the linear portion, the length direction extending substantially between the folded portion and the next folded portion.

2. A stent according to claim 1, wherein an axial length of any annular unit that includes the marker is greater than an axial length of any annular unit that does not include the marker.

3. A stent according to claim 2, wherein the annular units including the marker are disposed in axially opposite end portions of the stent.

4. A stent according to claim 2, wherein the annular unit including the marker is disposed in an axially intermediate portion of the stent.

5. A stent according to claim 2, wherein intermediate portions each running between one folded portion and a next folded portion in the linear portion comprise gentle S-shapes arrayed substantially in parallel in a state where the stent is radially contracted.

6. A stent according to claim 1, wherein the annular units including the marker are disposed in axially opposite end portions of the stent.

7. A stent according to claim 1, wherein the annular unit including the marker is disposed in an axially intermediate portion of the stent.

8. A stent according to claim 1, wherein an axial length of any annular unit that includes the marker is greater than an axial length of any annular unit that does not have the marker.

9. A stent according to claim 1, wherein the annular units including the marker are disposed in axially opposite end portions of the stent.

10. A stent according to claim 1, wherein the annular unit including the marker is disposed in an axially intermediate portion of the stent.

11. A stent according to claim 1, wherein intermediate portions each running between one folded portion and a next folded portion in the linear portion comprise gentle S-shapes arrayed substantially in parallel in a state where the stent is radially contracted.

12. A stent according to claim 1, wherein intermediate portions each running between one folded portion and a next folded portion in the linear portion comprise gentle S-shapes arrayed substantially in parallel in a state where the stent is radially contracted.

13. A stent according to claim 1, wherein the connection portions are connected to folded portions of adjacent annular units.

14. A stent according to claim 1, wherein the linear portions of the at least one annular unit, other than between the folded portion and the next folded portion, comprise substantially a same shape.

15. A stent according to claim 1, wherein drop-out prevention protrusions engage upper and lower surfaces of the marker.

16. A stent according to claim 1, wherein an opening angle of a folded portion of the annular unit provided with the frame portion is substantially equal to an opening angle of a folded portion of an annular unit of the plurality of annular units which does not include a frame portion.

17. A stent according to claim 1, wherein an axial length of an annular unit that includes the marker and an axial length of an annular unit of the plurality of annular units that does not include the marker comprises a ratio in a range of $L1:L2=1:1.2\text{-}1.6$, where L2 comprises the axial length of the annular unit that includes the marker and L1 comprises the axial length of the annular unit that does not include the marker.

18. A stent according to claim 1, wherein a connection portion of the connection portions connects a folded portion an annular unit of the plurality of annular units to an other folded portion of an other annular unit of the plurality of annular units.

19. A stent according to claim 1, wherein the connection portions are arrayed in each annular unit of the plurality of annular units such that the connection portions of an annular unit are circumferentially shifted from the connection portions of an other annular unit.

20. A stent according to claim 1, wherein the connection portions connect the annular units at a location which is other than a location of the frame portion.

* * * * *